(12) United States Patent
Nothias et al.

(10) Patent No.: US 9,623,044 B2
(45) Date of Patent: Apr. 18, 2017

(54) CHITOSAN HYDROGEL FOR REPAIRING NERVE TISSUE

(71) Applicants: UNIVERSITE CLAUDE BERNARD LYON I, Villeurbanne (FR); INSTITUT NATIONAL DES SCIENCES APPLIQUEES DE LYON, Villeurbanne (FR); UNIVERSITE JEAN MONNET, SAINT ETIENNE, Saint Etienne (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR); UNIVERSITE PIERRE ET MARIE CURIE (PARIS 6), Paris (FR)

(72) Inventors: Fatiha Nothias, Paris (FR); Sylvia Soares, Les Lilas (FR); Laurent David, Lyons (FR); Alexandra Montembault, Saint Etienne (FR)

(73) Assignees: UNIVERSITE CLAUDE BERNARD LYON I, Villeurbanne (FR); INSTITUT NATIONAL DES SCIENCES APPLIQUEES DE LYON, Villeurbanne (FR); UNIVERSITE JEAN MONNET, SAINT ETIENNE, Saint Etienne (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

(21) Appl. No.: 14/414,994

(22) PCT Filed: Jul. 16, 2013

(86) PCT No.: PCT/FR2013/051710
§ 371 (c)(1),
(2) Date: Jan. 15, 2015

(87) PCT Pub. No.: WO2014/013188
PCT Pub. Date: Jan. 23, 2014

(65) Prior Publication Data
US 2015/0174153 A1   Jun. 25, 2015

(30) Foreign Application Priority Data

Jul. 19, 2012  (FR) .................... 12 57006

(51) Int. Cl.
| | | |
|---|---|---|
| A61K 31/722 | (2006.01) |
| A61L 27/20 | (2006.01) |
| A61L 27/52 | (2006.01) |
| A61L 27/38 | (2006.01) |
| A61L 27/50 | (2006.01) |
| A61K 9/16 | (2006.01) |
| A61K 45/06 | (2006.01) |

(52) U.S. Cl.
CPC .............. *A61K 31/722* (2013.01); *A61K 9/16* (2013.01); *A61K 45/06* (2013.01); *A61L 27/20* (2013.01); *A61L 27/383* (2013.01); *A61L 27/3834* (2013.01); *A61L 27/50* (2013.01); *A61L 27/52* (2013.01); *A61L 2400/06* (2013.01); *A61L 2430/32* (2013.01)

(58) Field of Classification Search
None
See application file for complete search history.

(56) References Cited

U.S. PATENT DOCUMENTS

2010/0178345 A1* 7/2010 Hung .................... A61K 9/5026
424/487
2011/0052713 A1* 3/2011 Cho .................. A61K 47/48861
424/493

OTHER PUBLICATIONS

Agnihotri et al., Journal of Controlled Release, 2004; 100: 5-28.*
Vickers, Drugs Aging, 2002, 19(7): 487-494.*
Mayo Clinic website downloaded Mar. 24, 2016 from mayoclinic.org/diseases-conditions/alzheimers-disease/diagnosis-treatment/treatment/txc-20167132?p=1; 4 pages total.*
Small et al., Proc Natl Acad Sci USA, 2000; 97:6037-6042.*
Ransohoff, Nature Neuroscience 2012; 15: 1074-1077.*
Behan et al., Inflammopharmacology 18:265-290, 2010.*

(Continued)

*Primary Examiner* — Christina Borgeest
(74) *Attorney, Agent, or Firm* — Ladas & Parry LLP

(57) ABSTRACT

The present invention relates to chitosan hydrogel microparticles of a median size d50 comprised between 1 and 500 μm (obtained from a number distribution), the chitosan having a degree of acetylation of less than equal to 20% and its concentration in the hydrogel being comprised between 0.25 and 5% by weight based on a total weight of the hydrogel, for use in neuron regeneration and/or in the repair of the nervous system, advantageously of the central nervous system, and/or in the grafting of neurons and/or in the treatment of neurodegenerative diseases and/or in the treatment of paralyses.

Figure 1:
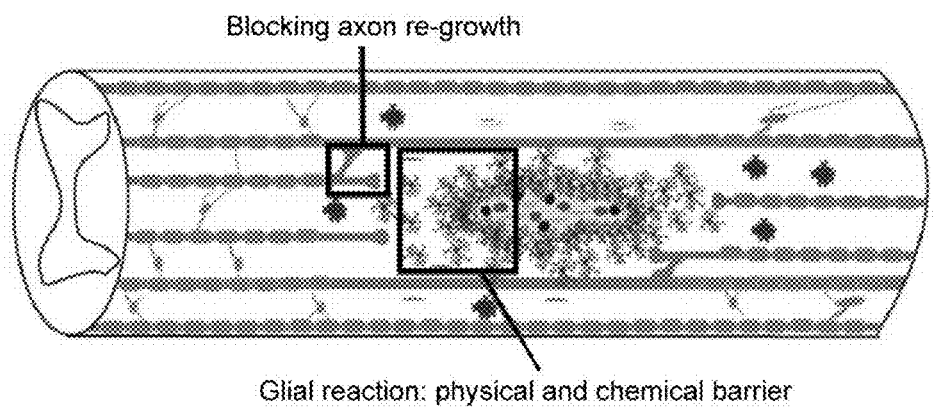

It also relates to an implant comprising an aqueous suspension of microparticles mixed with Schwann cells and/or stem cells and/or trophic factors.

9 Claims, 6 Drawing Sheets

(56) References Cited

OTHER PUBLICATIONS

Kim et al., Biotechnology Advances 2008; 26: 1-21.*
CN101112365, original document in Chinese; English translation attached; 18 pages total.*
Brunel et al., Langmuir 2008, 24, 11370-11377.*
Wu et al., Wound Repair Regen. 2007; 15 Suppl 1: S18-26.*
Montembault et al., Biomaterials, 2005; 26: 1633-1643.*
International Search Report dated Aug. 22, 2013, corresponding to International Patent Application PCT/FR2013/051710.
Cho et al.: "Chitosan nanoparticle-based neuronal membrane sealing and neuroprotection following acrolein-induced cell injury", Journal of Biological Engineering, vol. 4, No. 2, 2010, pp. 1-11.
Ying Yuan et al.: "The interaction of Schwann cells with chitosan membranes and fibers in vitro", Biomaterials, vol. 25, 2004, pp. 4273-4278.
Karin S. Staley et al.: "Biomaterial design strategies for the treatment of spinal cord injuries", Journal of Neurotrauma, vol. 27, 2010, pp. 1-19.

* cited by examiner

CHITOSAN HYDROGEL FOR REPAIRING NERVE TISSUE

This application is a 371 of PCT/FR2013/051710, filed on Jul. 16, 2013, which claims priority to French Application No. 1257006, filed Jul. 19, 2012.

The present invention relates to the general field of axon regeneration through a glial scar in particular produced by trauma of the central nervous system (CNS) or peripheral nervous system (PNS) such as traumatic injuries of the spinal cord. Traumatic injuries of the spinal cord (SC) lead to paralyses, loss of sensation and chronic pain. In the large majority of cases in humans (like in rodents in experimental models), these injuries are expressed by rupture of nerve connections between the brain and the remainder of the body, followed by gradual neurodegeneration from the site of the lesion and formation of a cavity surrounded by a glial scar. The whole forms both a physical and chemical barrier for regrowth of axons. The chemical barrier is due to significant production by non-neuronal cells of inhibitory molecules (cytokines, proteoglycans (i.e. CSPG (Chondroitin Sulphate ProteoGlycans) of the extracellular matrix (ECM) of chemorepellent molecules). Other inhibitory molecules are derived from myelin (myelin-derived protein Nogo-A, MAG (Myelin-Associated Glycoproteins) and Omgp (Oligodendrocyte myelin glycoprotein)); they are exposed in the ECM following demyelinization of axons. The supply of trophic factors unfortunately remains low. Thus, repair of the broken neuronal network is blocked.

In addition to these inhibitory effects, the bioavailability of trophic factors promoting axon survival and regeneration is quite limited. As a comparison, the peripheral nervous system is quite able to be subject to repair and axon regeneration, after a traumatic injury, by means of the fast inflammatory response of macrophages and the action of Schwann cells (myelinating cells of the PNS), promoting rapid removal of cell debris and myelin. However, in the case of severe lesions, the complete regeneration is sometimes limited because of the difficulty of guiding the fibers towards the suitable peripheral targets.

Nevertheless, the CNS of mammals is provided with great neuronal plasticity. Thus, after a partial lesion of the EM, the unaffected axons may be subject to rearrangements and may participate in functional recovery, essentially related to growth of collateral extensions (or "sprouting"). These observations are those which have triggered since then, the development of therapeutic strategies for repairing the damaged nervous system (Nothias F (2011) *Stimulating axon regrowth, in "Régénération nerveuse, des cellules souches aux interfaces cerveau-machine"*, (nerve regeneration, stem cells at the brain-machine interfaces) special issue magazine, BIOFUTUR VOL 30/322 JUNE 2011, pp. 36-40).

Many experimental models have been developed for stimulating axon regrowth in struggling against the inhibitory action of the proteins contained in the glial scar:

Injection of IN1 antibodies for antagonizing the inhibitory effect of certain components of myelin (Nogo, MAG and Omgp) which share the same receptor at the neuron, Nogo-A.

Degradation by a specific enzyme (ChABC, a chondroitinase of the ABC type) at the extracellular matrix of the proteoglycan CSPG, also an inhibitor of axon growth.

Peptide injection mimicking the effect of adhesion molecules which are favourable for axon growth. This is the case of a peptide mimicking the function of the oligosaccharide PSA (polysialic acid) which, in the brain, is related to the adhesion molecule NCAM (neural cell adhesion molecule). The NCAM during development is rich in PSA and plays a primordial role for the growth and bundling of the fibre bundles.

Genetic engineering for reducing the glial reaction in particular that of astrocytes.

Supplying neurotrophic factors (BDNF (Brain-derived neurotrophic factor), NT3 (Neutrophin 3)) or of cells having a trophic effect on the neurons in order to increase the survival rate and also for promoting axon regrowth.

Substitution of the lesioned tissue with a transplantation of embryo neurons, stem cells, Schwann cells (myelinating cells of the peripheral nervous system) or further ensheathing cells of the olfactory bulb for guiding and optionally myelinating the axons.

In the majority of the experimental models for repairing traumatic spinal cord (SC), only a small number of axons regenerate and very few of them manage to cross the whole of the lesion site. Two major obstacles subsist which have to be removed:

(i) it is necessary to control the time window for efficient axon regrowth: one must act as quickly as possible after the lesion;

(ii) the spatial organization of the lesion site should be taken into account in order to not only provide a permissive environment but also a spatial organization contributing to guiding the regrowth.

Bioactive and biodegradable, natural or synthetic polymeric materials have also been used for generating a physical and mechanical support for axon growth, and/or for mimicking the biological effect of an extracellular matrix. Collagen, a major component of the extracellular matrix, in the form of hydrogel is the material which has been the most used. However, while its implantation in the PNS has resulted in better axon regeneration, at the CNS level alone its combination with a supply of trophic factors has shown partial functional improvement. Further, the polymeric implants used should generally have a shape allowing guidance of the axon regeneration (e.g.: tubular implants in the form of bridges).

Chitosan is a bioactive and biodegradable polymer known in the state of the art, notably for its biocompatibility, bio-resorbability and healing properties. The properties have been used inter alia in medicine and surgery.

Chitosan is a polymer of natural origin obtained by deacetylation of chitin. Chitin is a biopolymer with a high molecular weight, non-toxic and biodegradable, and is with cellulose the most widespread polysaccharide in nature. Chitin consists of a linear chain, the structure of which contains recurrent units of the glucosamine (GLcN) and N-acetylglucosamine (GLcNAc) type bound through a $\beta,(1->4)$ bond. Extraction of chitin from crustacean shells and/or from squid endoskeletons, is mainly accomplished via a chemical route, and then transformation by deacetylation of the chitin in hot concentrated soda allows chitosan to be obtained. Because of its biocompatibility with human tissues and its healing properties, chitosan has demonstrated its efficiency in various physical forms such as gels, powders or films, in various products such as bandages, plasters, artificial skin, corneal bandage, surgical suture threads which naturally resorb after healing, but also in bone repair or in the repair of cartilage (Montembault et al. *Biochimie*, 88, 2006, pages 551-564) and in dental surgery, in implants or in the healing of gums, in well-tolerated contact lenses.

Chitosan has also been used as an intrathecal implant under vertebrae in vertebral columns of rats (Kim Howard et al. *Journal of Biomedical Materials Research,* 15 Jun. 2011, Vol. 97A, no. 4, pages 395-404). However, the implant used had the shape of a non-porous sheet and the applied test was intended to show that this biopolymer was biocompatible and may therefore be used for long-term applications in the repairing of spinal cord. This document therefore does not describe any axon regrowth in the case of the use of chitosan in the form of non-porous sheets. Further, it is highly likely that such a regrowth is impossible considering the shape of the chitosan used.

In the review article of Karin S. Straley et al., (*J Neurotrauma.* 2010 January; 27(1): 1-19 doi: 10.1089/neu.2009.0948), it is indicated that chitosan scaffoldings were used for transferring grafts of viable nerves, neural stem cells, and neural progenitor cells into the vertebral column of rats, which promoted axon regeneration. However, in these applications, the chitosan is never used alone and is always in the form of blocks. Further, chitosan is mentioned among many other biomaterials such as collagen, poly-α-hydroxy acids, hyaluronic acid and fibrin, without chitosan being indicated as particularly of greater interest than these other materials.

Generally, the hydrogels used in the development of therapeutic strategies for the spinal cord or peripheral nerve, have been essentially designed as tubes of large diameter, as a support for adhering and confining cells which are favorable for axon regrowth like Schwann cells. Moreover, several of these studies used chitosan mixed with proteins or polysaccharides such as gelatin, collagen, poly-D-lysine or further agarose; chitosan having the lowest concentration in the mixture (Zuidema et al., 2011, *Acta Biomateriala* 7:1634-1643; Karin et al., 2010, *journal of Neurotrauma,* 27:1-19; Annabi et al., *Tissue Eng Part B Rev.* 2010, 16: 371-383; review of Yang T-L, 2011, *Int. J. Mol. Sci,* 12, 1936-1963; Pfister L A et al., 2007, *J Biomed Mater Res A.* 80:932-7).

The publication of Youngnam Cho et al. in Biological engineering 2010 4, 2, entitled <<chitosan nanoparticle-based neuronal membrane sealing and neuroprotection following acrolein-induced cell injury" describes the use of nanoparticles, particles of complexes formed with chitosan and dextran sulfate or sodium tripolyphosphate, into which is either incorporated hydralazine or not and evaluates their use in an in vitro model of a neuro-protective effect. Taking into account the size of the particles described in this document, which is of 250-300 nm, it is demonstrated that the particles are internalized in cells cultivated in vitro (as illustrated in FIG. 9).

Surprisingly, the inventors have discovered that microparticles of chitosan hydrogel may be used successfully as an implant in axon regeneration, provided that the chitosan has a low acetylation degree, without it being needed to give the implant a shape allowing guidance of the axons, such as tubes. Indeed, the implant based on microparticles has an open and porous physical shape, a more significant one than what a block may provide. The results obtained in rats show that these hydrogel microparticles may be successfully used in particular in the repair of spinal cord lesions since the axons cross the lesion site over a long distance (at least 3 to 4 mm). The inventors have discovered that the introduction of chitosan reduces the reaction of astrocytes, both a morphological and molecular reaction. Indeed, these cells are known for rapidly reacting upon introduction of an element which is not part of the nervous tissue, they form a barrier with their extensions so as to generate a boundary between the damaged tissue and the healthy tissue. They also secrete molecules, most of which are inhibitory for axon growth (for example CSPG). Moreover, the inventors have discovered that even astrocytes may migrate through the implant and their extension at the boundary of the lesion is associated with the axons which re-grow, a phenomenon which is described during the development of the nervous system. Such an effect on astrocytes and axons has never been demonstrated in the experimental models used before: the number of axons obtained in these models was insufficient for invading the whole of the lesion, around 10% thereof. The inventors have discovered that chitosan not only has adhesive properties but also attractive properties. They noted that retraction of axons is highly reduced, which explains the numerous fibers which regrow through the lesion.

The present invention therefore relates to chitosan hydrogel microparticles with a median size d50 for a number distribution comprised between 1 and 500 µm, the chitosan having an acetylation degree of less than or equal to 20% and its concentration in the hydrogel being comprised between 0.25 and 5% by weight based on the total weight of the hydrogel, for use in neuronal regeneration and/or in the repair of the nervous system (either the central or peripheral system), advantageously of the central nervous system (in particular the spinal cord), and/or in the grafting of neurons and/or in the treatment of neurodegenerative diseases (such as Alzheimer's or Parkinson's disease) and/or in the treatment of paralyses. Advantageously, the repair or the regeneration or the treatment of paralyses is subsequent to a lesion, in particular a traumatic lesion of the nervous system (either central or peripheral such as severe lesions of the peripheral nerve), or more advantageously of the central nervous system, in particular of the brain or, preferably of the spinal cord.

Indeed, the microparticles are implanted, either at the lesion, in particular the traumatic lesion, in order to fill this lesion, or at the location where axon regrowth or repair or grafting should take place. The microparticles are therefore advantageously implanted by injection, even more advantageously by surgery.

The treatment may not be subsequent to a traumatic lesion like in the case of neurodegenerative lesions. These neurodegenerative lesions are not due to a physical impact. They cause a loss of neurons in specific sites. The axons from other regions are then without any target cells and therefore cannot play their role. On the one hand, the implantation at the lesion of the microparticles according to present invention may generate a favorable environment for stimulating their regrowth towards other undamaged neurons. On the other hand, the neurons connected initially to the lesioned region experiencing a deficit of relevant input information, the implantation of particles may also stimulate the regrowth of collateral parts of neighboring axons.

Chitosan used within the scope of the invention is obtained by deacetylation of chitin in an alkaline medium (Robert G A F *Chitin Chemistry,* Macmillan Press Ltd Ed., London, 1994, chitin being the polymer of the structure of exoskeletons of arthropods (A. Domard and G. Chaussard; *New Approach in the Study of the Production of Chitosan from Squid Pens: Kinetics, Thermodynamic and Structural Aspects. In Adv. Chitin Sc.* 5, 1-5. 2002; K. Kurita et al.; *Squid Chitin as a Potential Alternative Chitin Source: Deacetylation Behaviour and Characteristic Properties. J. Polym. Sci. Part A* 31, 485-491. 1993), endoskeletons of cephalopods (H.-M. Cauchie; *An Attempt to Estimate Crustacean Chitin Production in the Hydrosphere. In Adv. Chitin Sci.* 2, 32-39. 1997) or further cell walls of certain fungi or algae. Therefore, except for the cases where the acetylation degree is 0%, chitosan is a copolymer of the two following monomers: 2-acetamido-2-deoxy-D-glucopyranose and 2-amino-2-deoxy-D-glucopyranose bound through a glycoside bond β,(1->4). In particular, the chitosan is available commercially, for example at Mahtani Chitosan by deacetylation of squid or shrimp chitin.

The chitosan which may be used within the scope of the present invention has an acetylation degree of less than or equal to 20%, i.e. comprised between 0 and 20%. Indeed, if a larger acetylation degree is used, the inventors noticed that the chitosan does not allow axon regeneration and further induces a significant inflammatory reaction. Advantageously, the chitosan which may be used within the scope of the present invention has an acetylation degree comprised between 0 and 10%, advantageously less than 5%, more advantageously comprised between 1 and 4%, in particular of about 3%. The degree of acetylation further has an influence on the bioresorbability of chitosan, when the latter is implanted in an organism, i.e. its degradation in the organism, in particular the human body, which results in its disappearance, its degradation products being metabolised or excreted by the organism. Indeed, the more the acetylation degree increases, the higher are the kinetics of bio-degradation and bio-resorption. The latter will therefore be selected depending on the targeted application. Within the scope of the present invention, the acetylation degree of the chitosan is measured by using the proton NMR technique, following the methodology of Hirai (Asako Hirai, Hisashi Odani, Akio Nakajima, *Polymer Bulletin* (1991) Volume: 26, Issue: 1, Publisher: Springer, Pages: 87-94).

In a particular embodiment, the molar mass of the chitosan is greater than 180,000 g/mol, advantageously greater than 200,000 g/mol, advantageously greater than 300,000 g/mol, more advantageously less than 1,000,000 g/mol, even more advantageously less than 600,000 g/mol, in particular of about 450,000 g/mol. The inventors noticed, surprisingly that high molar masses give the possibility of obtaining a hydrogel not very concentrated in chitosan while limiting the inflammatory response, and promoting bio-resorbability of the hydrogel.

By hydrogel, in the sense of the present invention is meant a viscoelastic mass (having a complex shearing modulus $G^*=G'+jG''$ such that $G'>10G''$ over a frequency range of more than 1 decade) including at least 80% by mass of water, preferably at least 90% by mass of water, and preferentially at least 95% by mass of water. There exist two categories of hydrogels: chemical hydrogels and physical hydrogels. A hydrogel is said to be a physical hydrogel, when the interactions responsible for the inter-chain cross-linking are of a physical type, and are notably hydrogen bonds and/or hydrophobic interactions as opposed to a so called chemical hydrogel in which the inter-chain interactions are of the covalent bond type.

Within the scope of the present invention, the concentration of the chitosan in the hydrogel is comprised between 0.25 and 5% by weight based on the total weight of the hydrogel, advantageously less than 4% by weight based on the total weight of the hydrogel, advantageously greater than 0.5% by weight based on the total weight of the hydrogel, in particular comprised between 1 and 3% by weight based on the total weight of the hydrogel, more particularly of about 2.5% by weight based on the total weight of the hydrogel. The inventors noticed that when the solution of chitosan has a concentration of less than 0.25% by weight, it is not possible to gel the solution so as to obtain a macroscopic hydrogel. Further, above 5% by weight of chitosan in the solution, its dissolution becomes difficult and the obtained viscosity of the solutions makes the elaboration of materials difficult.

In an advantageous embodiment of the present invention, a physical hydrogel of chitosan will be used. The advantage of this type of hydrogel is that it does not contain any chemical cross-linking agent which may be toxic. The formation of such hydrogels is for example described in the following publications, to which reference may be made: A. Montembault; C. Viton and A. Domard in *Rheometric study of the gelation of chitosan in a hydroalcoholic medium. Biomaterials,* 26(14), 1633-1643, 2004 and Montembault A, Viton C, Domard A, *Rheometric study of the gelation of chitosan in aqueous water without cross-linking agent, Biomacromolecules,* 6 (2): 653-662, 2005.

In particular the physical hydrogel according to the present invention is obtained via the aqueous or hydro-alcoholic route, advantageously via the aqueous route, such as for example the method comprising the following successive steps:
  preparing a solution of chitosan with a concentration comprised between 0.25% and 5% by weight based on the total weight of the solution, by mixing purified and freeze dried chitosan and of an aqueous solution of acetic acid;
  gelling by contact of the obtained solution with ammonia vapours; and
  washing the hydrogel obtained in order to remove ammonia and the salts formed during the gelling. The advantage of the aqueous route is that the hydrogels obtained are rapidly biodegraded in the human body.

The chitosan hydrogel microparticles which may be used within the scope of the present invention are characterized by a median size d50 comprised between 1 and 500 μm (for a number distribution), advantageously between 5 and 300 μm, advantageously between 10 and 50 μm, in particular of about 20 μm. The median size d50 of the microparticles is for example measured by an observation carried out with a phase contrast optical microscope of the Zeiss brand (Axiovert 200M), with the image acquisition software package Linkys32. The distribution of the sizes of the hydrogel microparticles may be obtained by image processing with the software package ImageJ (www.rsbweb.nih.gov/ij), or as described in C. Igathinathane et al. (*computers and electronics in agriculture* 63 (2008) 168-182).

The chitosan microparticles having the desired median size d50 may be obtained by milling the hydrogel, in particular by using a homogenizer ULTRATURAX of brand IKA (operating at a speed of rotation of 11,000 rpm for 3×10 s and stopping for 30 seconds between the sequences) and recovering the microparticles of a satisfactory size for example by centrifugation (for example 13,000 rpm for 3 minutes with an apparatus of the Sigma 3K30 type of the brand Bioblock Scientific).

Advantageously, the method according to the present invention includes a sterilization step, in particular with an autoclave, for example at 121° C. for 20 minutes, before recovering the microparticles.

Figure 5:
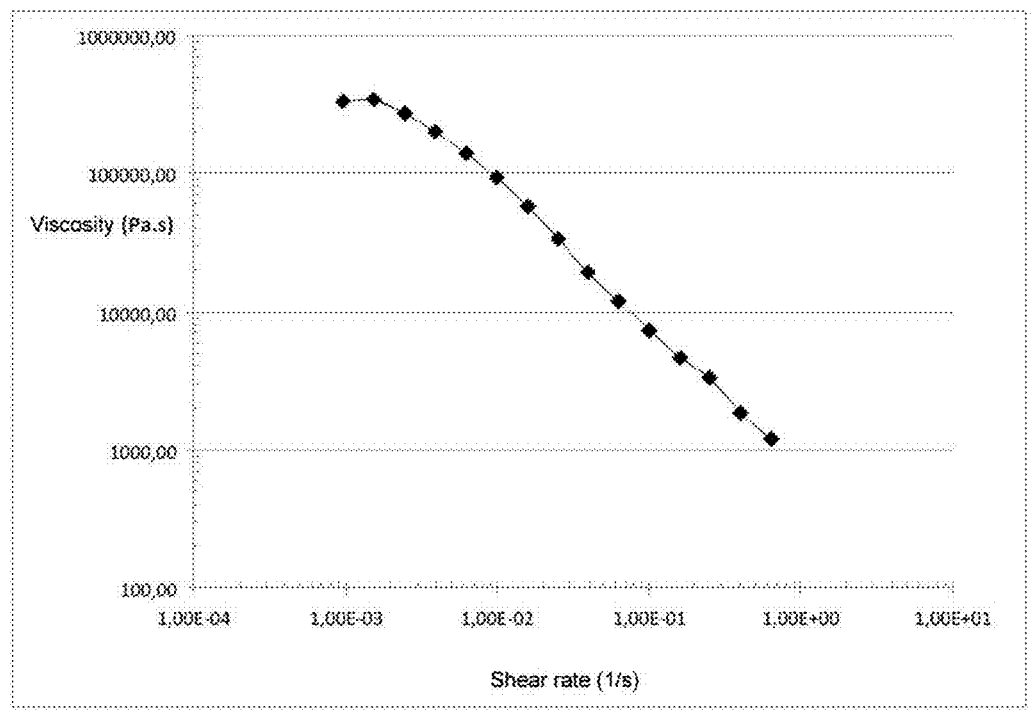

In a particular embodiment of the present invention, the microparticles according to the invention are found in the form of an aqueous suspension, advantageously having a viscosity of more than 1000 Pa·s, advantageously greater than 10,000 Pa·s, even more advantageously greater than 100,000 Pa·s, in particular of about 330 kPa·s, (measured in a continuous mode at 22° C.) for a shearing rate of 0.001 s$^{-1}$, advantageously measured by cone-plane rheometry with a rheometer with imposed stress (Advanced Rheometer AR2000 of the brand TA Instruments). It is therefore this suspension which will be implanted. In this case, the implant used comprises an aqueous suspension containing the hydrogel microparticles according to the present invention. Advantageously, the suspension is injectable or implantable by surgery. For example, the characteristic value of viscosity of the suspension may be 330 kPa·s after centrifugation at 13,000 rpm for 3 minutes from a hydrogel with a 2.5% concentration of chitosan of a molar mass of 450,000 g/mol (FIG. 5).

This suspension therefore has to be sufficiently liquid in order to be directly injected into the lesional site where the axons have been cut by the impact which has damaged the nervous tissue and sufficiently thick for remaining confined in the implantation location. Also the advantage of this suspension being injectable is to allow repair in the case of a contusion which does not necessarily generate the rupture of the duramater (the membrane which protects the nervous tissues just below the bone (vertebrae or skull)). In the case of brain trauma, the impact may damage an area in depth and an injection may avoid inducing an additional significant lesion. This may also be applied in a neurodegenerative lesion (i.e. which is not necessarily due to a traumatic impact but resulting from neuronal death). Thus, this suspension rather has the form of a slurry.

In another embodiment of the present invention, the microparticles according to the invention are mixed with Schwann cells and/or stem cells and/or trophic factors.

This suspension may be made by evaporating water from the centrifugation pellet containing the microparticle according to the present invention obtained by the method for making microparticles indicated above, advantageously in order to obtain a viscosity greater than 1,000 Pa·s (measurement of the viscosity of the suspension in a continuous mode at 22° C. for a shear rate of $0.001$ s$^{-1}$).

This evaporation may for example be accomplished by depositing the suspension present in the centrifugation pellet on a glass plate and by leaving it to dry for a few minutes (for example 5 to 10 min) at room temperature (around 20° C.) and in free air until the required consistency is obtained for grasping it with small tweezers and depositing it in the site of the lesion during surgery. This is valid in the case of a traumatic lesion of the spinal cord. In the case of injection, the pellet may be re-suspended in physiological liquid or artificial cerebrospinal fluid.

The present invention further relates to an implant, comprising an aqueous suspension of microparticles as defined above and the Schwann cells and/or stem cells and/or trophic factors. The addition of the cells may be accomplished one or two hours after implantation, for the time for them to adhere to the microparticles given that chitosan has adhesive properties which the inventors moreover verified in vitro, on cell cultures. Advantageously, this implant does not contain any chondrocytes.

Advantageously, this implant is an implant intended for the nervous system, in particular the central nervous system, advantageously for the spinal cord. Therefore, it should not cause any inflammatory reaction in the implantation location, additional to that generated by the lesion impact.

The advantage of the microparticles according to the present invention is that they provide a suitable surface for both cell and axon adhesion on the one hand and on the other hand that the axons may use the inter-particulate porosity (between the microparticles of the suspension) for invading the lesion site. Indeed, the inventors have already verified that cultivated neurons grow their neurites (among other axons) on a substrate consisting of the same chitosan suspension proposed here for in vivo implantation. In order to grow, the axons need a tie for generating an extension force.

The suspension or the microparticles may also be used in plurimembrane systems such as for example the chitosan plurimembrane fibres described in patent application WO2009/044053 for forming implants, for example at the traumatic lesion.

The present invention further relates to a method for neuronal regeneration and/or repair of the (either central or peripheral) nervous system, advantageously of the central nervous system (in particular the spinal cord), and/or grafting neurons or precursors of neural cells (glia and neurons) and/or treatment of neurodegenerative diseases (such as Alzheimer's or Parkinson's disease, or further multiple sclerosis) and/or ischemic lesion and/or treatment of paralyses comprising the implantation of microparticles according to the present invention in a patient in need of such a treatment, in particular at an advantageously traumatic lesion in order to fill this lesion, or at the location where axon growth and repair or grafting has to take place. Advantageously, this implantation is accomplished by deposition, injection or surgery.

The present invention will be better understood in the light of the figures and examples which follow.

FIG. 1 illustrates the diagram of a traumatic lesion in the spinal cord. This scheme shows that around the initial lesion site, the axons which were cut, are blocked and do not grow again (many of them retract and degenerate over time). The astrocytes migrate and surround the lesion so as to form the physical and chemical barrier, without however migrating into the inside of the lesion site. Healing is often followed by the formation of a cavity (for example observed in humans and in rats).

Figure 2:
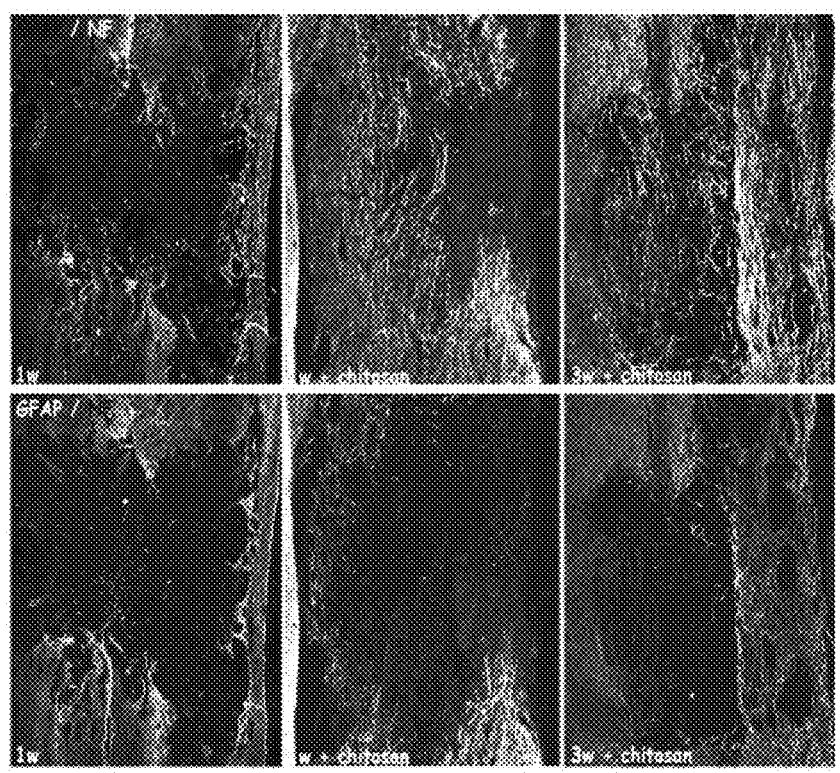

FIG. 2 illustrates photographs of double immunofluorescences made on adult rat spinal cord sections, 1 week (1 w, figures on the left and in the middle) and 3 weeks (figures on the right, 3 w) after hemisection, with implantation of microparticles according to Example 1 of the present invention (+chitosan, figures in the middle and on the right) or without any implantation (the left most). The upper photographs show the marking of the neurofilaments (NF) which show the presence of axons of the neurons. The lower photographs (GFAP) show the astrocytes (glial cells of the central nervous system). It should be noted that at one week, many axons arrive from the host tissue and have already invaded the lesion site, both on the rostral side (towards the brain) and on the caudal side (towards the tail of the animal). Compare the density of the axons at one week between the section with a single lesion and a section with one lesion+chitosan. By examining the figures after 1 and 3 weeks of lesion+chitosan, it may be noted that the number of axons has further increased over time and that the regrowth is accomplished over long distances. It should also be noted that the glial reaction remains low.

Figure 3:
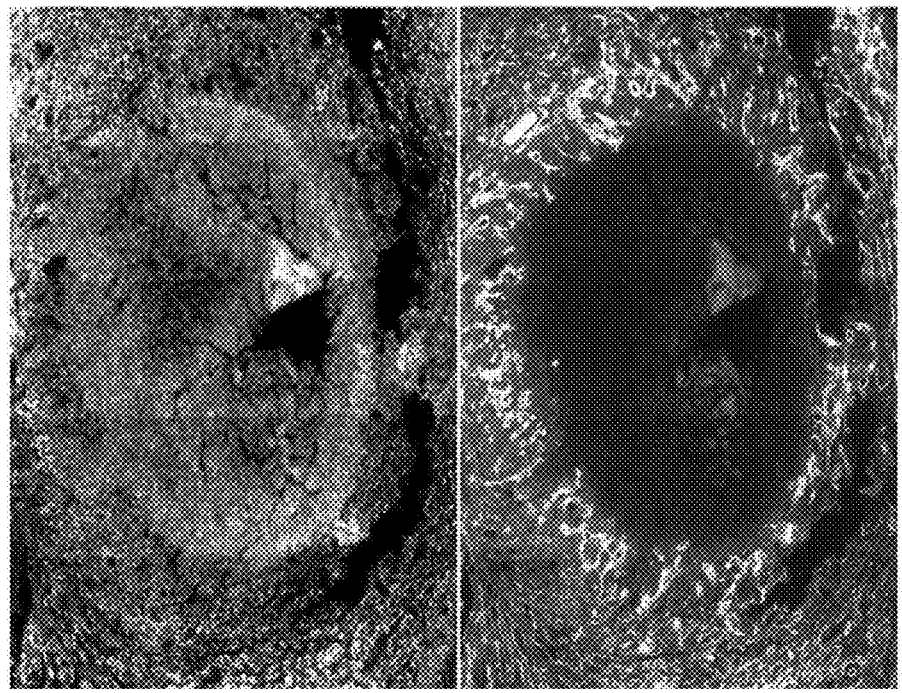

FIG. 3 illustrates a photograph of an adult rat spinal cord section, 4 weeks after hemisection and implantation of chitosan physical hydrogel microparticles having a high acetylation degree (35%) at the site of the traumatic lesion. The left photograph includes double labelling with the anti-ED1 of macrophages and the right photograph an immunolabeling of laminin which shows the blood microvessels and therefore vascularization. This type of implant generates a strong inflammatory reaction, blocks axon regrowth and even the migration of endothelial cells (cells at the origin of blood vessels) through the implant, while at a low degree of acetylation, vascularization is noted inside the implant of microparticles.

Figure 4:
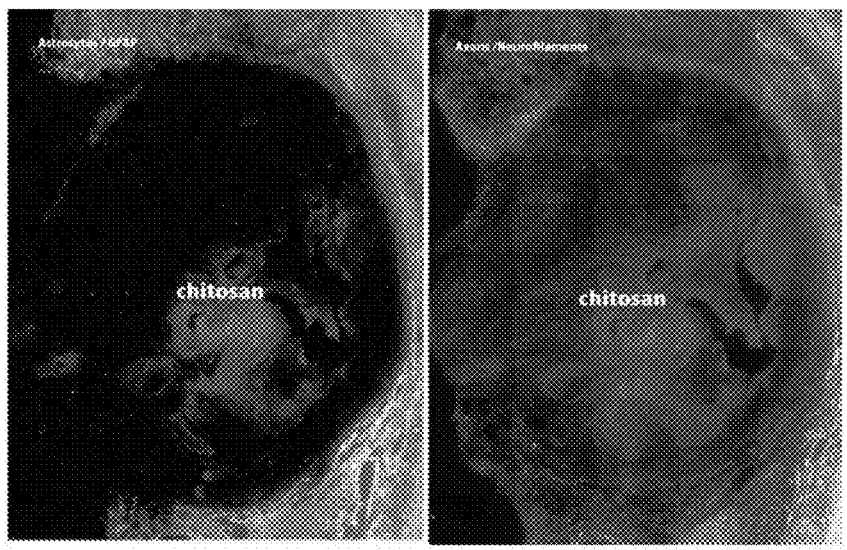

FIG. 4 illustrates a photograph of an adult rat spinal cord section, 4 weeks after hemisection and implantation of a chitosan physical hydrogel block with a low degree of acetylation (3%) at the site of the traumatic lesion. The left photograph includes immunolabeling with an anti-GFAP of the astrocytes and the right photograph an immunolabeling of the axons with an anti-Neurofilament. Even if the astrocyte glial reaction and the inflammatory reaction are reduced, the axons in proximity to the implant, are found blocked at the boundary and do not grow again through the implant.

FIG. 5 illustrates the time dependent change curve of viscosity (in Pa·s) of a suspension of microparticles according to Example 1 of the invention (obtained after centrifugation at 1300 revolutions/minutes for 3 minutes, the hydrogel comprising 2.5% by weight of chitosan with a degree of acetylation of 3%) versus the shearing rate (in $s^{-1}$), the viscosity being measured in a continuous mode at 22° C. by cone-plane rheometry with a rheometer with imposed stress Advanced Rheometer AR2000 of the TA Instruments brand.

Figure 6:
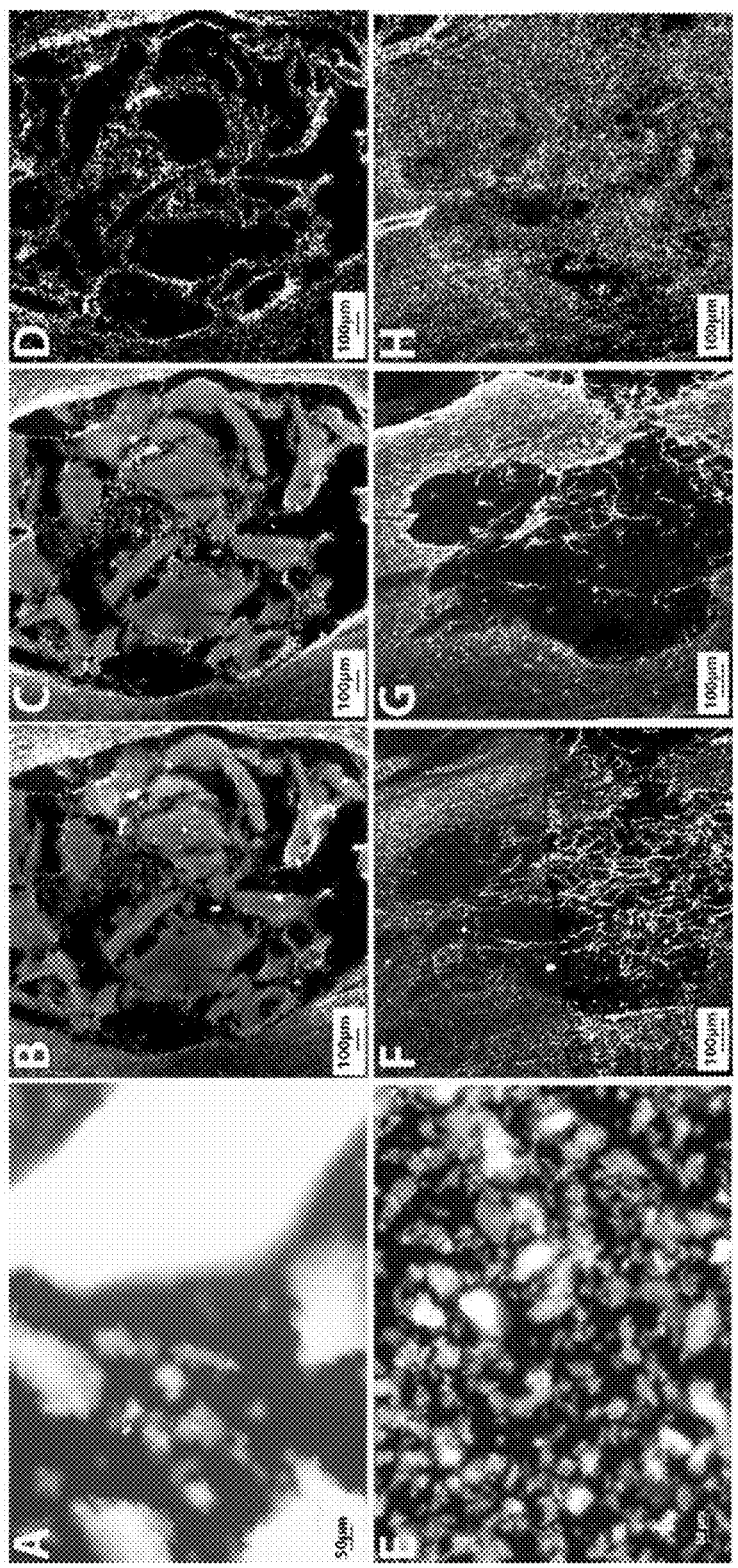

FIG. 6 allows observation in phase contrast optical microscopy on the first line, of a dispersion of physical chitosan hydrogel micro-particles according to Comparative Example 3 and on the second line according to an example made according to Example 1

A—This photograph allows measurement of the size distribution of the gel microparticles before implantion, with a large dimension exceeding 500 microns for a majority fraction of particles, therefore corresponding to a d50 of more than 500 µm. Four weeks after implantation of this formulation in the spinal chord of an adult rat having been subject to hemisection (B-D), it may be noted that the polymer remains very opaque in phase contrast optical microscopy; very few axons (specific labeling of the axons in B), very few astrocytes (specific labeling of the astrocytes in C) invade the implant. Further, the labeling of the nuclei of the cells (specific labeling of the cell nuclei in D) shows that very few cells invade the implant, with non-colonized areas occupied by microgels.

E—This photograph allows measurement of the size distribution of the gel microparticles before implantion, with an apparent median size of fragments comprised between 20 and 50 microns. Four weeks after implantation of this formulation in the spinal chord of an adult rat, having been subject to hemisection (F-H), it may be noted that the lesion is invaded by many cells (specific labeling of the cell nuclei in H), among which astrocytes (specific labeling of the astrocytes or star-shaped cells in G), the astrocyte reaction which surrounds the implant is not very marked (G), unlike what may be observed with chitosan microparticles in FIG. 6.-C. Further many axons (specific labeling of axons in F) invade the implant.

Figure 7:
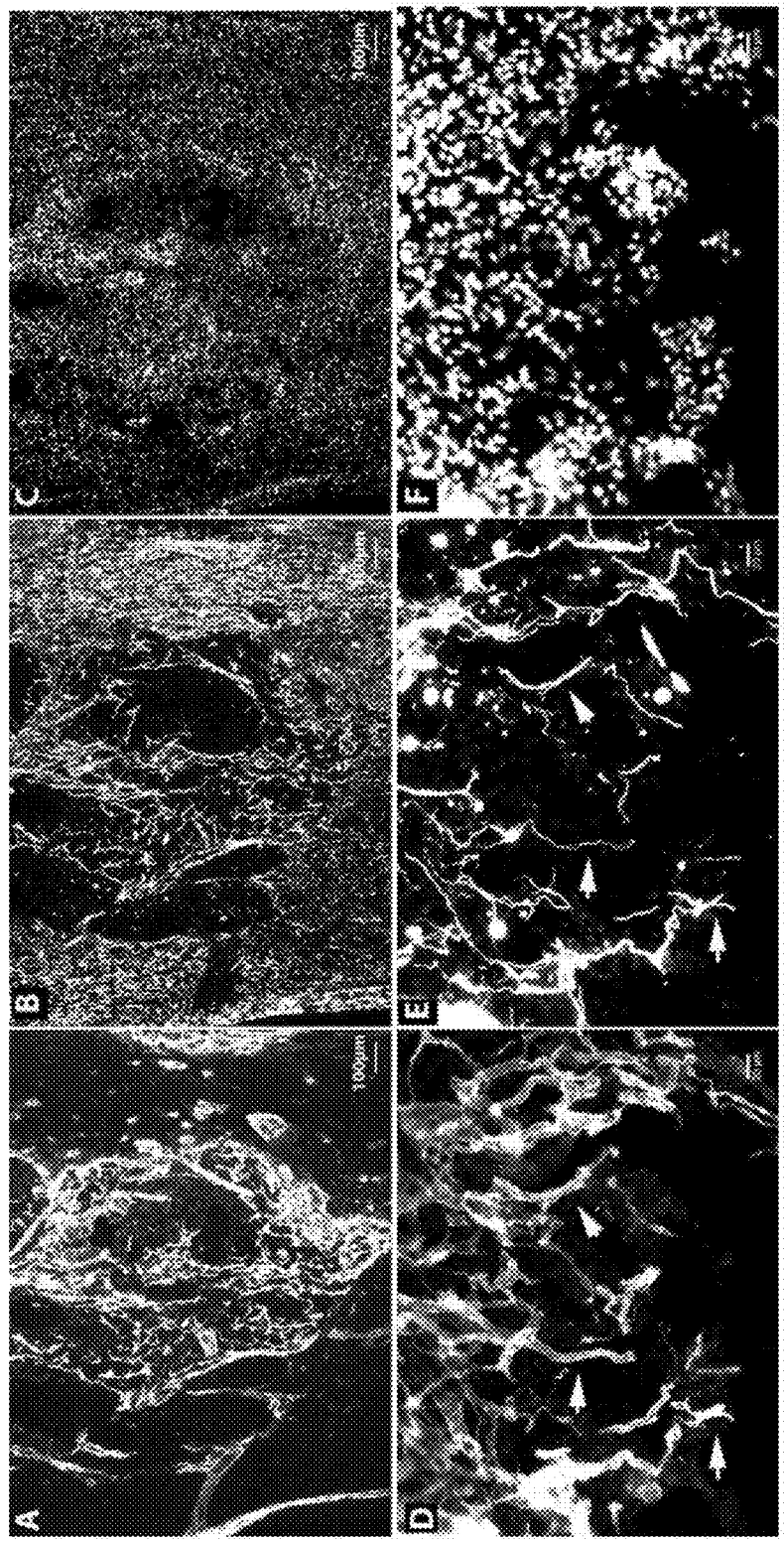

FIG. 7 shows photographs of a spinal cord section of an adult rat showing the time-dependent change in the lesion after implantation of chitosan microparticles according to the invention of FIG. 6-E, 4 weeks after the lesion and implantation. A-C: triple labelings showing highly organized neo-vascularization (specific labeling of the vessels in A) in the implant, accompanied by strong re-growth of axons (specific labeling axons in B) and by massive invasion by cells (specific labeling of cell nuclei in C). D-E: high magnification achieved in the implant which show the association (arrows) of the axons (D) with the newly formed microvessels (E) in the implant.

Figure 8:
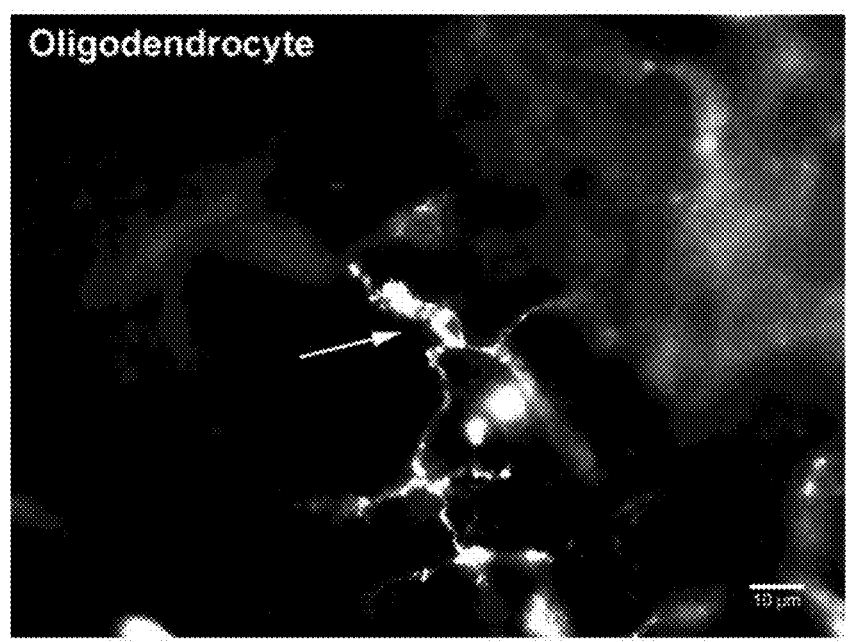

FIG. 8 shows a photograph of a spinal cord section of an adult rat showing the time-dependent change in the implant after implantation of chitosan microparticles according to the invention of FIG. 6-E. Among the cells which colonize the implant, oligodendrocytes (arrow) are noted, cells which may myelinate the regenerating axons, as well as re-establish the nerve impulses.

Example 1

Manufacturing Microparticles According to the Present Invention

Dissolution of the chitosan with a degree of acetylation of 3% from squid chitin marketed by Mahtani Chitosan, in an aqueous solution of acetic acid (introduced in stoichiometric amounts relative to the amine functions) so as to obtain a solution containing 0.5% by weight of chitosan.

Filtration on filters of 3 microns, 1 microns and 0.45 microns.

Precipitation with soda or ammonia until a pH of 14 is attained.

Recovery of the precipitate by centrifugation.

Washing with deionized water until the pH of the washing waters is neutral for removing the salts.

Freeze drying the washed precipitate in order to obtain a dry product.

Preparing a solution of chitosan with a molar mass of 450,000 g/mol at 2.5% by weight based on the total weight of the solution from the precipitate and from pure water (Versol®).

Gelling by contact of the solution in Petri dishes with diameters of a few centimeters, in the presence of ammonia vapours (72 h).

Washing of the hydrogels with deionized water for removing ammonia.

Renewing the operation for a total of 7 washes.

Checking that the neutrality pH is attained.

Milling of the hydrogels with the ULTRATURAX apparatus of brand IKA (operating at a speed of rotation of 11,000 rpm for 3×10 s and stopping for 30 seconds between the sequences).

Sterilizing the microparticles of the hydrogel with an autoclave (121° C. for 20 minutes).

Centrifugation (13,000 rpm for 3 minutes with an apparatus of the Sigma 3K30 type of brand Bioblock Scientific) so as to recover the sterilized microparticles having a median size d50 of about 20 µm.

These microparticles are then used for making an aqueous suspension with a minimum viscosity of 1,000 Pa·s. For this, the centrifugation pellet obtained is deposited on a glass plate which is dried in the open air at room temperature for a few minutes. Partial drying occurs which allows an increase in the viscosity up to a viscosity of 330 kPa·s measured at 22° C. for a shear rate of 0.001 $s^{-1}$ (measurement in a continuous mode by cone-plane rheometry with a rheometer with imposed stress Advanced Rheometer AR2000 of the brand TA Instruments) as indicated in FIG. 5.

Comparative Example 1

Manufacturing Microparticles of Chitosan Physical Hydrogel with a Large Degree of Acetylation The same method as the one used in example 1 is used (the microparticles obtained have the same median size d50 as in example 1, the chitosan content is the same as in Example 1, as well as the viscosity of the obtained suspension) except that the initial chitosan has a degree of acetylation of 35%. In order to obtain such a degree of acetylation, the chitosan was re-acetylated from a chitosan of low degree of acetylation (3%) purchased from Mahtani Chitosan and dried as indicated in example 1 in a hydro-alcoholic medium, as described in the following publication: *Biomacromolecules*. 2001 2(3):765-72. *Relation between the degree of acetylation and the electrostatic properties of chitin and chitosan*. Sorlier P, Denuzière A, Viton C, Domard A.

Comparative Example 2

Manufacturing of Chitosan Physical Hydrogel Blocks with a Low Degree of Acetylation The same method is used as the one described in example 1 except that there is no milling, centrifugation and partial drying step on a glass plate. The obtained physical hydrogel is directly sterilized before being cut out in the intended dimensions.

Comparative Example 3

Manufacturing Microparticles Having a d50 of More than 500 µm

The method for obtaining these particles is identical with the one of Example 1, except that the concentration of chitosan in the initial hydrogel is 3.5% by weight of chitosan based on the total weight, and that the gel milling period is only 10 seconds instead of 3×10 seconds.

Test of Repair of a Traumatic Lesion in the Spinal Cord

For these tests, the lesion of the spinal cord is produced by lateral thoracic hemisection Th8/Th9 of the EM of an adult rat followed by a sampling of the lateral dorsal portion (2 to 3 mm) of the exposed segment. This type of lesion is found between the last thoracic segment and the first lumbar segment. In the case of hemisection, this generates hemiplegia of the posterior paw on the same side of the lesion. Control rats are subject to same type of lesion but are left to heal without any implant.

The implants were introduced by surgery immediately after producing the lesion and reducing bleeding caused by the trauma. The tested implants are of three types:

An amount representing about 2-3 mm$^3$ of the aqueous solution of microparticles according to the present invention (obtained according to example 1), An amount representing about 2-3 mm$^3$ of the aqueous solution of chitosan hydrogel microparticles with a high degree of acetylation (obtained according to the comparative example 1

Or a block of about 2-3 mm$^3$ cut out in the chitosan physical hydrogel obtained according to the comparative example 2.

All in all 24 animals (12 with lesion+implant and 12 control animals: only the lesion) were analyzed.

At variable post-lesion times, the animals are deeply anesthetized and perfused from the heart with a fixative (4% of paraformaldehyde in 0.1M phosphate buffer, PBS) for fixing the tissue of interest. Spinal cord sections are then carried out between 1 (n=8) and 3 (n=8) to 4 (n=8) post-lesion weeks, so as to practice morphological and immunohistological analysis.

After dissection and sampling, the tissues of interest (spinal cord) are cryo-protected with sucrose in order to produce 30 mm sections in the cryostat which are mounted on plates and kept at −80° C. until their use in histology.

After permeabilization (0.3% Triton in PBS) and saturation of the specific sites (NGS (normal goat serum), 10% in PBS), the sections are incubated in the solution of primary antibodies diluted in NGS 5%-PBS, overnight at 4° C. Incubation with the secondary antibodies coupled with suitable fluorochromes is carried out for 2 h at room temperature, away from light. After rinsing, the plates are mounted with Mowiol. The labelings are analyzed by fluorescence microscopy.

As illustrated in FIG. 1, a mechanical lesion in the spinal cord causes the formation of a physical and chemical barrier which surrounds the lesion and blocks the regrowth of the lesioned axons.

FIG. 2 shows, in the three lower photographs, astrocytes (glial cells of the central nervous system) which are activated following the lesion and which are responsible for the formation of the barrier illustrated in FIG. 1. FIG. 2 shows, in the first upper photograph, that the axons of the neurons do not penetrate the lesion delimited by the barrier, at 1 week without any chitosan implant.

The implantation of chitosan microparticles according to the present invention on the other hand allows massive growth of the axons through the lesion, at 1 and 3 weeks (note the strong fibrillary labeling at the centre of the lesion and the rectilinear orientation of the axon regrowth through the lesion site) as shown by the two last upper photographs, on the right (NF) of FIG. 2.

Morphological and immunohistological analyses therefore clearly show and in an impressing way, the changes which occur after implantation of the microparticles according to the invention in the lesions EM, as compared with a single lesion without any implant:

The astrocyte glial reaction is clearly reduced. The cell body of the astrocytes is less atrophied, their processes are finer and longer, very often oriented towards the centre of the lesion. This makes the intact tissue-lesion boundary less sharp, by lack of accumulation of the astrocyte processes surrounding the lesional site, therefore reduction in the physical barrier. This demonstrates that there exists a great compatibility between the host tissue and the implant. Moreover, this morphological aspect of the astrocytes—orientation of their extensions towards the epicenter of the lesion—is a sign that these cells rather play a favorable role for the regrowth of axons. Moreover, at the inlet of the implant, extensions of the astrocytes associated with the regrowing axons with the same orientation (parallel) and this over a long distance are often observed. A significant observation which reinforces this compatibility is the presence of astrocytes (identification of their cell body) within the implant, proving that these cells have also migrated inside the implant. It therefore appears that the chitosan microparticles according to the invention form a permissible substrate for this type of glial cells.

In spite of the large size of the lesion (3 to 4 mm wide), the introduction of the microparticles does not increase the inflammatory (macrophage) reaction and the cystic cavity is reduced.

By nuclear labeling with DAPI, it was possible to note that the microparticles of chitosan hydrogel are populated with many cells: macrophages/microglia; the astrocytes as indicated above; endothelial cells which form new vessels. On this subject, the implant is well vascularized and the network or the cytoarchitecture of the neo-vascularization is accomplished in a more organized way (as testified by FIG. 6). In the implant and in the host tissue surrounding the site of the lesion, many precursors of oligodendrocytes (cells which myelinate the axons of the central nervous system) have also been identified, which shows that in the presence of the implant, the proliferation of the endogenous NPCs (multipotent neural precursor cells) is stimulated and their differentiation to the phenotype of oligodendrocytes is promoted. This observation is important in so far that it is known that subsequent to a lesion, demyelination occurs even at the axons which are not directly damaged. This suggests that by stimulating the proliferation and differentiation of oligodendrocytes, the remyelination repair may occur and, accordingly the neuronal electric activity is re-established (as testified by FIG. 8). Such observations therefore predict the benefit of the chitosan hydrogel microparticles according to the invention for treating multiple sclerosis.

Most remarkable is the presence of a significant number of axons which cross the lesion site, as testified by FIG. 2. These axons penetrate into the implant both upstream and downstream from the lesion. FIG. 2 also testifies that the regrowth capacity is ensured over a long distance. These observations are noted at 1 and 4 post-lesion weeks, and have been confirmed beyond 3 post-lesion months. It is also interesting to note that the axon regrowth in the implant is associated with vascularization (as testified by FIG. 7). Indeed, it was shown, in a very small size lesion model and by two-photon imaging in vivo on the anesthetized animal, that the axons which attempt to regenerate are guided (or assisted) at the beginning of their regrowth by the surrounding vessels (Dray C, Rougon G, Debarbieux F, Proc Natl Acad Sci USA. 2009 Jun. 9; 106(23):9459-64. doi: 10.1073/pnas.0900222106. Epub 2009 May 21). In the present case, this association (on a fixed tissue) is observed after several weeks. It should be noted that the in vivo approach on the animal after a severe lesion of the spinal cord is not feasible.

The whole of these observations at the implant testifies that the chitosan microparticles according to the invention form a permissive and attractive substrate, highly favorable for restoring traumatic spinal cord. Its local implantation in the site of the lesion generates a favorable environment for the whole of the neural cells and proves to be a permissive and attractive substrate for axon growth. Moreover, the invasion of the implant by endogenous cells and establishment of vascularization give the possibility of regenerating a tissue bridge between the rostral portion (towards the head) and caudal portion and prevents formation of necrosis which, in the case of the single lesion, results in the formation of a cavity surrounded by an astrocyte and molecular boundary for protecting the healthy tissue from propagation of the damage. Such an effect has never been demonstrated, even in strategies combining other approaches.

On the contrary, FIG. 3 shows, on the left photograph, an inflammatory reaction (with the anti-ED1) (note the immunomarking crown around the chitosan) and on the right photograph that the vascularization (by immunolabeling of laminin) is limited to the outside of the chitosan. Thus, this proves that axon regrowth is blocked and that the astrocyte and inflammatory reactions are significant. The significant inflammatory reaction also generated very strong neo-angiogenesis and a larger secondary lesion.

Finally, FIG. 4 shows that the microstructure of the implant has a highly sensitive impact on the tissue response. Indeed, it is necessary to use microparticles and not a bulk or block monolithic hydrogel: in the latter case, axon regrowth is blocked at the boundary of the chitosan block by the presence of the material.

Thus, these tests therefore show quite surprisingly that a suspension of physical chitosan hydrogel microparticles with a low degree of acetylation gives the possibility of stimulating and guiding axon regrowth in traumatic lesions of the spinal cord, without causing any inflammation.

The invention claimed is:

1. A method of neuron regenerating and/or repairing of the nervous system, and/or grafting of neurons or precursors of neural cells, and/or treatment of neurodegenerative diseases, and/or treatment of ischemic wounds and/or treatment of paralyses, the method comprising:
   administering, to a mammal in need thereof, an effective amount of chitosan hydrogel microparticles;
   wherein said microparticles have a median size d50, obtained from a number distribution, of from 1 to 500 µm;
   wherein said chitosan has a degree of acetylation of less than or equal to 20%;
   wherein the concentration of chitosan in the hydrogel is from 0.25 to 5% by weight, based on the total weight of the hydrogel; and
   wherein the microparticles are administered subsequent to a traumatic lesion of the nervous system of the mammal, which is a traumatic lesion of the spinal cord.

2. The method according to claim 1, wherein the median size d50 of the microparticles is from 5 to 300 µm.

3. The method according to claim 1 wherein the degree of acetylation of the chitosan is less than 5%.

4. The method according to claim 1, wherein the concentration of the chitosan in the hydrogel is less than 4% by weight, based on the total weight of the hydrogel.

5. The method according to claim 1, wherein the hydrogel is a physical chitosan hydrogel, such that interactions responsible for the inter-chain cross-linking in the hydrogel are of a physical type.

6. The method according to claim 1, comprising administering the microparticles in an aqueous suspension having a viscosity greater than 1000 Pa·s measured in a continuous mode at 22° C. for a shear rate of $0.001$ s$^{-1}$.

7. The method according to claim 6, wherein the aqueous suspension is in an injectable form or an implantable form.

8. The method according to claim 6, comprising mixing the microparticles with a member selected from the group consisting of Schwann cells, stem cells, trophic factors, and a combination thereof.

9. The method according to claim 1, wherein the mammal is a human being.

* * * * *